United States Patent [19]

Spears

[11] Patent Number: 5,133,360
[45] Date of Patent: Jul. 28, 1992

[54] SPEARS RETRIEVER

[76] Inventor: Colin P. Spears, 3376 Tyrrell Pl., Glendale, Calif. 91206-1444

[21] Appl. No.: 665,543

[22] Filed: Mar. 7, 1991

[51] Int. Cl.$^5$ ............................................. A61B 10/00
[52] U.S. Cl. ..................................... 128/754; 606/170
[58] Field of Search ....................... 128/749, 751, 754; 606/167, 170

[56] References Cited

U.S. PATENT DOCUMENTS

| | | |
|---|---|---|
| 185,902 | 1/1877 | Fallows . |
| 1,293,351 | 2/1919 | Creasey . |
| 1,422,066 | 7/1922 | Vafiades . |
| 1,568,008 | 5/1925 | Thomas . |
| 1,609,456 | 12/1926 | Boyle . |
| 2,117,278 | 5/1938 | Ainsworth . |
| 2,188,362 | 1/1940 | Krilow . |
| 2,263,531 | 11/1941 | Kevorkian . |
| 2,541,542 | 12/1946 | Perez . |
| 2,583,577 | 1/1952 | Kingsbury . |
| 2,683,312 | 12/1952 | Dover . |
| 2,751,864 | 8/1953 | Parker . |
| 3,125,883 | 3/1961 | Wollner . |
| 4,174,715 | 11/1979 | Hasson . |
| 4,310,969 | 1/1982 | Cannizzaro . |
| 4,461,305 | 7/1984 | Cibley ................................. 128/754 |
| 4,651,752 | 3/1987 | Fuerst . |
| 4,785,826 | 11/1988 | Ward . |
| 4,926,877 | 5/1990 | Bookwalter . |

FOREIGN PATENT DOCUMENTS 198770   4/1965   Sweden ............................. 128/754

*Primary Examiner*—Max Hindenburg
*Attorney, Agent, or Firm*—Cushman, Darby & Cushman

[57] ABSTRACT

A biopsy instrument is provided which has a retractable cutting wire or filament looped external to the innermost surface of the distal end of the tissue cutting cylinder. Forceful retraction of the cutting wire will cause displacement and closure of a loop of wire over the distal margin of the cored tissue biopsy, thus freeing the biopsy specimen in its entirety from its original locus and allowing removal of the entire cored biopsy from the body substantially without stretching the specimen along its length.

22 Claims, 4 Drawing Sheets

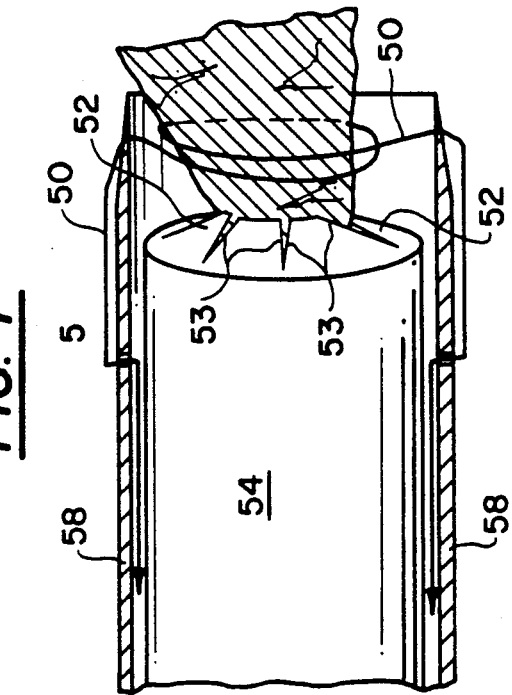
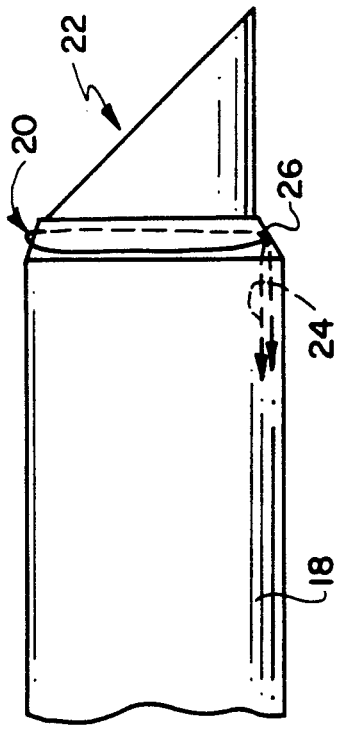
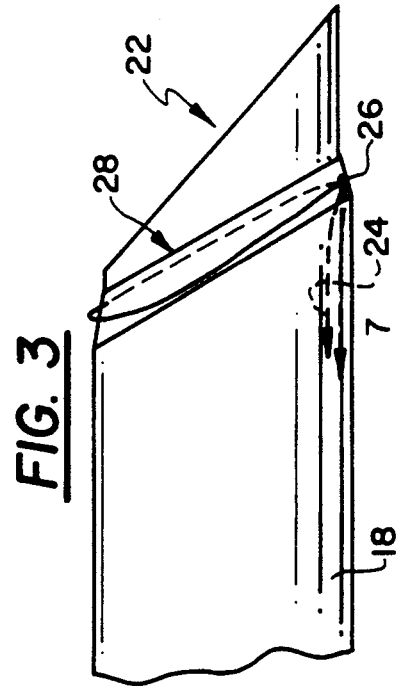
FIG. 1 (PRIOR ART)
FIG. 7
FIG. 2
FIG. 3

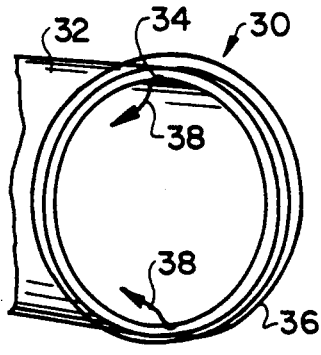
FIG. 4A
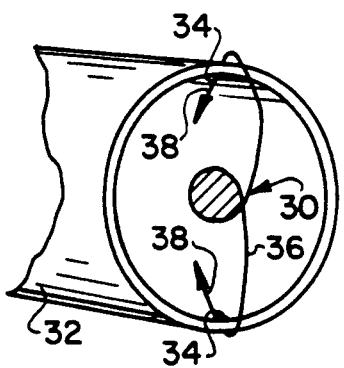
FIG. 4B
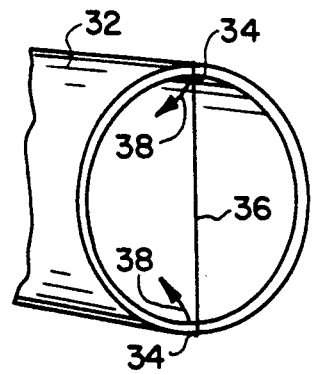
FIG. 4C
FIG. 5
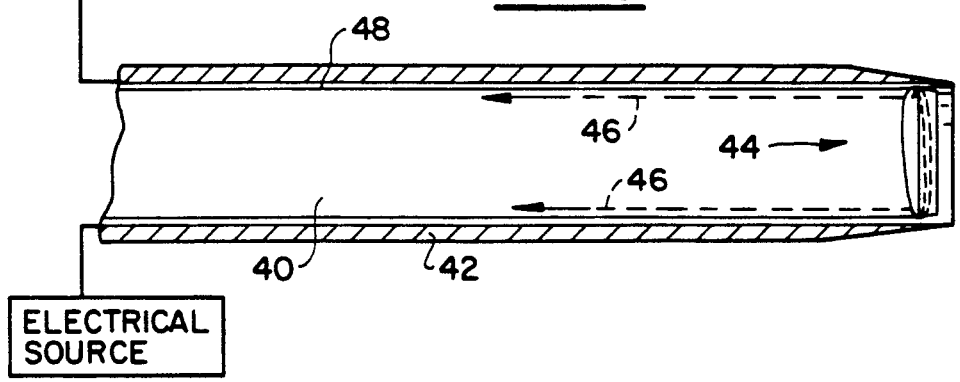
FIG. 8
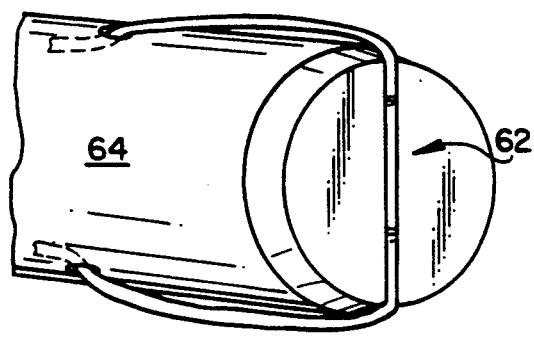

SPEARS RETRIEVER

BACKGROUND OF THE INVENTION

1. Field of the Invention

The present invention relates to biopsy instruments and, in particular, to a biopsy instrument with which a cored tissue sample can be severed to allow easy retrieval.

2. Description of the Related Art

One of the most frequently used instruments for biopsy, particularly biopsy of the skin, is the so-called Keyes punch. For example, the Baker/Cummins or Baker Biopsy Punch manufactured by a division of Key Pharmaceutical, Miami, Fla.

An example of a conventional punch biopsy instrument 10 is shown in FIG. 1. That instrument has a tubular cutting end 12 formed, for example, from metal and mounted to a plastic handle 14. By advancing the biopsy instrument 10 against the tissue to be sampled, a cylinder of tissue is cored by the razor-sharp beveled circular tip 13. The instrument 10 may be advanced as deep into the tissue as permitted by the length of the metal cylinder, typically by using a gentle pressure combined with a twirling rotation action effected by the practitioner manipulating the handle.

A deficiency of the above-noted instrument is that after the tissue sample has been cored, removal of the cylindrical sample is difficult as the same remains connected to the surrounding tissue at its base. Indeed, currently no device or system has been provided which can advantageously and simply cut the still attached distal segment of tissue. At present, general practice is to use tweezers or the like to pull the exposed end of the tissue core, thus stretching the tissue cylinder. The deepest margin accessible to a surgical blade or scissors is then cut in order to remove the tissue sample from the body of the patient. It is generally not possible to sever the cored tissue sample at its base without cutting the non-cored adjacent tissue.

Thus, the use of the conventional punch biopsy instrument has several disadvantages, including distortion of the major portion of the tissue biopsy from the pulling action of the tweezers or like instrument, which can potentially lead to histological artifacts and incomplete removal of the cored tissue. Indeed, often less than one half of the cored tissue is actually attained in practice. Finally, fragmentation and subdivision of the biopsy with loss of orientation of margins of the fragments is possible.

SUMMARY OF THE INVENTION

It is an object of the invention to overcome the limitations of the conventional punch biopsy instrument by providing a retractable cutting wire or filament mounted to the exterior surface of the distal end of the tissue cutting cylinder to allow severance of the distal margin of the cored tissue.

In accordance with the instrument of the invention, forceful retraction of the cutting wire will cause displacement and closure of a loop of wire over the distal margin of the cored tissue biopsy, thus freeing the biopsy specimen in its entirety from its original locus and allowing removal of the entire cored tissue segment from the body without stretching the specimen along its length. Accordingly, the entire cored biopsy specimen can be removed while minimizing histological distortion.

In accordance with invention, the loop of cutting material can be provided so as to facilitate uniform severing of the cored segment and to provide a support structure for facilitating removal of the tissue sample. Furthermore, in accordance with modifications of the basic concept of the invention, cauterization of severed vessels, cooling and/or freezing of the cored sample, and/or acceleration of the cutting action to ensure a clean, complete cut of the tissue are possible. The device of the invention can also be advantageously used in applications other than simple tissue biopsy including hair transplantation, suturing and ligation and can be advantageously employed in combination with other devices to enable biopsy of deep structures.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings all of which form a part of this specification, wherein like reference numerals designate corresponding parts in the various figures.

BRIEF DESCRIPTION OF THE DRAWINGS

FIG. 1 is a cross-sectional view of a conventional punch biopsy instrument;

FIG. 2 is an elevational view, partly in cross-section, of a biopsy instrument formed in accordance with the present invention;

FIG. 3 is an elevational view showing an alternate embodiment of the tip of an instrument in accordance with the invention;

FIGS. 4A–4C are perspective views of a preferred cutting loop provided in accordance with the present invention;

FIG. 5 is an elevational view, partly in cross-section, of a further alternate embodiment of the present invention;

FIG. 7 is an elevational view of the assembly of FIG. 6A showing engagement of the tissue segment in accordance with one aspect of the invention; and FIG. 8 is a perspective view of a further embodiment of the invention.

DETAILED DESCRIPTION OF THE PRESENTLY PREFERRED EXEMPLARY EMBODIMENTS

Figure 6A:
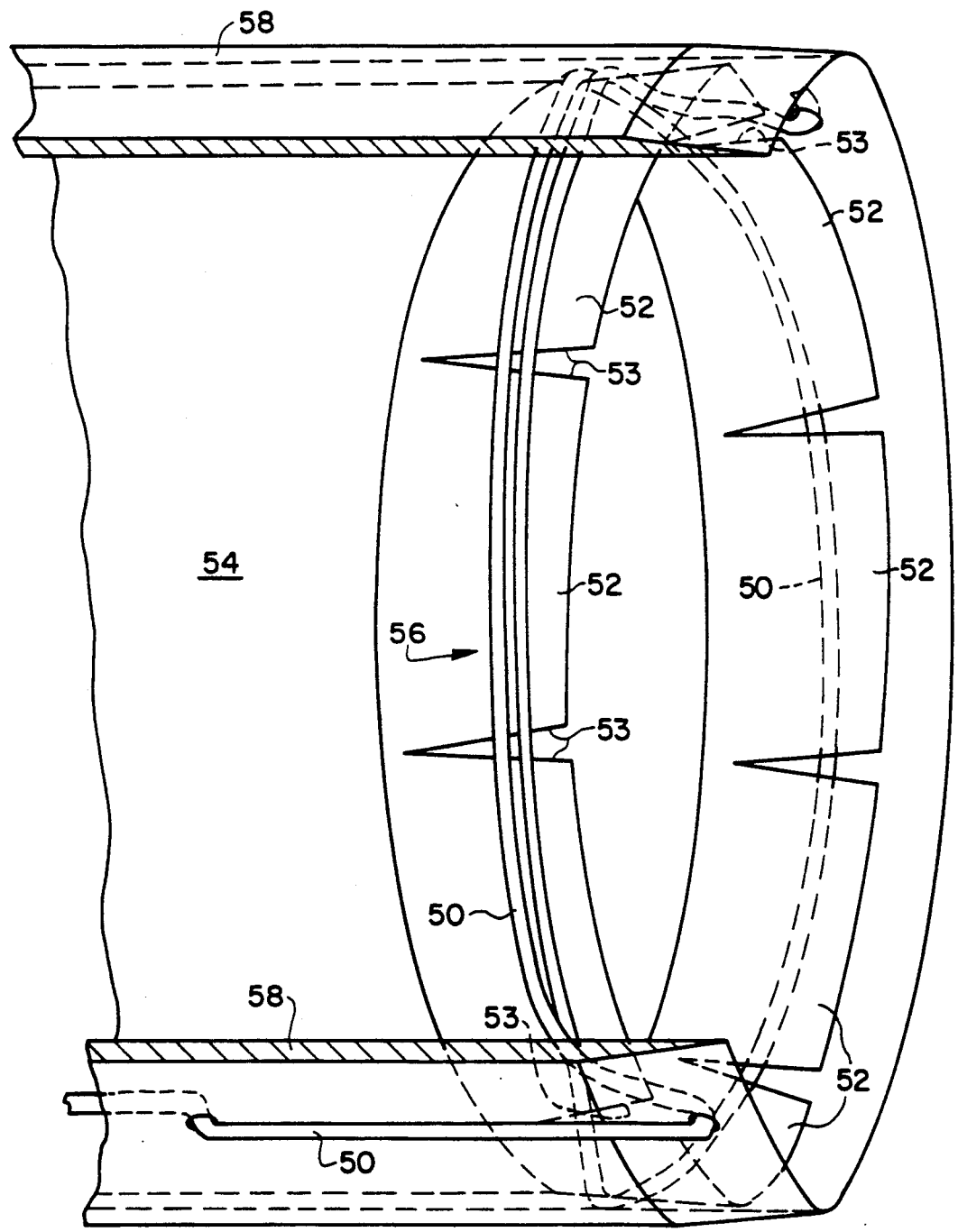
FIG. 6A is an enlarged perspective view of a trocar assembly provided in accordance with the present invention.

An exemplary embodiment of the present invention is shown in FIG. 2. As can be seen, the biopsy instrument 16 of the invention includes a coring cylinder 18 with a thread-like element 20 looped about the exterior surface thereof. The term cylinder as used in the specification and claims is not necessarily limited to a cylindrical element having a circular cross-section. Indeed, the cutting tip provided in accordance with the invention could be virtually any hollow cutting shape although, when the instrument is to be rotated during the cutting process, a circular cross-section is preferred to minimize trauma to the tissue. Where the cutting of the tissue is effected by a simple distal motion of the cutting instrument, however, it is to be appreciated that other cross-sectional shapes such as, for example, a square, a triangle, a hexagon or the like, could be employed.

As will become apparent hereinbelow, a retraction force on the cutting filament or wire 20 will cause displacement and closure of the loop over the distal margin of the cored tissue biopsy. This frees the biopsy specimen in its entirety and allows removal of the entire cored biopsy from the body without stretching the specimen along its length.

Where the biopsy instrument of the invention is utilized to obtain a sample of tissue which is not located at the surface or otherwise exposed for sampling, the coring cylinder 18 of the invention may be used in combination with a stylet or obturator 22 as schematically shown in FIG. 2. The sharp distalmost tip of the obturator protrudes distally from the trocar to present a needle-like point. The entire biopsy assembly 16 can be advanced under direct or radiographic observation up to the site of a planned tissue biopsy. Indeed, by cutting and displacing tissue, the obturator 22 allows insertion of the entire assembly to virtually any depth within the body. The obturator 22 is then removed and the trocar 18 is advanced under longitudinal pressure together with a twirling motion if necessary to a desired depth of tissue, e.g. 1-3 centimeters. Indicia may be provided to indicate depth of insertion of the biopsy instrument. Because the thread-like filament 20 provided in accordance with the invention is mounted to the exterior surface of the cutting cylinder 18, insertion and removal of the obturator 22 will not dislodge the filament 20 and the filament 20 will not engage and disrupt or be disrupted by the tissue sample cored by the cylinder 18.

While in the illustrated embodiment the stylet or obturator 22 has an off-center distalmost point it is to be understood that any suitable stylet or obturator could be provided in accordance with the invention, particularly depending upon the part of the body in which the instrument is to be used. Thus, a centrally disposed distal cutting point could be provided without departing from the invention.

Once the desired tissue sample has been cored by the instrument of the invention, the longitudinal end or ends 24 of the filament 20 are pulled by the operator to cause the filament 20 to slide over the distalmost tip of the biopsy instrument, thereby encircling the deepest end of the cored tissue sample, engaging the same, and severing it as the loop of the filament is closed. The trocar 18 is ultimately withdrawn from the body, with the tissue sample enclosed within its distal length.

In accordance with the invention, the filament 20 may be threaded as shown in FIG. 2 so that one or both longitudinal ends 24 of the filament enter a single aperture 26 provided in the exterior surface of the cutting cylinder 18 or so that each longitudinal end extends through spaced-apart apertures. For certain loop configurations, as described more fully below, the apertures may be disposed on opposite sides of the distal tip of the trocar. Further, one of the longitudinal ends can be fixedly coupled to the distal end of the trocar so that pulling only one end of the filament or wire actuates closure of the loop and severing of the tissue.

As is apparent, if a single aperture is provided, pulling on one or both longitudinal ends of the filament will effect complete removal of the filament following the cutting operation. Where spaced-apart apertures are provided, the filament will not be fully removed from the instrument unless only one end is pulled and the second end is free.

As shown in FIG. 3, in accordance with an alternate embodiment of the invention, the distal tip of the cutting cylinder 18 is inclined as at 28 so that the tip is shorter in length on the side opposite the side having the aperture(s) for receiving the longitudinal end(s) of the filament 20. Such an inclined configuration ensures that the cutting loop will easily slip off the end of the cylinder 18 when one or both longitudinal ends of the filament 20 are pulled. In that regard, the curvature of the distal tip of the shorter, opposite side can be such as to cause initial resistance to retraction of the ends of the cutting filament. This will cause a marked increase in tension in the filament prior to movement of the loop over the distal edge of the cutting cylinder. Thus, when the wire is ultimately released from the distal tip, there will be an accelerated movement of the loop. As such the cutting filament will impinge with a sufficient force onto the distal margin of the cored biopsy specimen to initiate the cut. Indeed, this rapid, forceful entry of the loop of material into the tissue will facilitate clean severance of the tissue.

The surface of the metal tip of the biopsy instrument can be coated or otherwise treated as desired so as to control the coefficient of friction thereof. For example, a teflon or similar coating can be provided to maintain a low coefficient of friction for a portion or all of the distal tip of the cutting filament. Likewise, if desired, portions of the surface of the cutting cylinder can be roughened in any suitable manner to increase friction to thereby maintain the cutting filament in place before pulling the proximal ends of the filament to release the filament and sever the tissue.

The cutting filament provided in accordance with the invention can be, for example, a fine filament-type wire which is either polymeric, metal or fibrous. Such filaments, which are generically and interchangeably referred to herein as either filament or wire although not necessarily limited to a metallic material or a single strand, must be fine enough to cut the tissue, strong enough not to break under the required pressure (1 to 20 pounds of force), flexible enough not to kink or catch at the aperture in the distal tip of the cutting cylinder or snag on a portion of the tissue due to kinking, and have a low enough surface coefficient of friction to enable slippage of the loop when a pulling force is exerted on the ends. The ordinary artisan will readily appreciate suitable materials exhibiting the foregoing characteristics. Furthermore, the filaments of the invention can be twisted, braided, knotted or otherwise multi-stranded materials. For example, double, triple or quadruple strand braided wire, cord or like filaments could be employed. An advantage of a multi-stranded filament is that the surface bumps or irregularities of the thus braided or twisted filaments will act as teeth of a saw which will facilitate severance of the tissue by the loop as it is closed. An example of a suitable stainless steel wire is about 0.0063 inches or less in diameter, alloy 304, soft temper, for example that manufactured by Western Wire and Cable Company. An example of a plastic material is 0.006 inch or narrower caliber plastic leader material of the type used for fishing, such as that manufactured by Maxima Manufacturing Company.

Moreover, the cutting wire provided in accordance with the present invention can be of any desired cross-section, not simply a circular cross-section as is typical of single filaments. Indeed, a wire may have, for example, a triangular cross-section which would present three cutting edges whereby cutting can be ensured, irrespective of the orientation of the filament. Indeed, triangular cutting wire may be an ideal shape owing to the effect that it always presents a cutting edge no matter how it is rotated. A braid or twist of three triangular strands, for example, would advantageously provide further cutting and strength characteristics. The cable may further be constructed from a mix of different shapes, e.g., a central core which is, for example, round, surrounded by a plurality of triangular or star-shaped wires to present a plurality of cutting edges about the periphery of the filament.

The cutting filament is threaded, as noted above, so as to loop about the exterior surface of the cutting cylinder. In the embodiment of FIG. 2, the loop is provided so as to close to thereby sever the tissue sample across the diameter of the deepest end thereof. The filament 20 is threaded through an aperture 26 provided in the exterior surface of the cutting element 18 and can be returned through suitable aperture(s) (not shown) to the exterior surface of the trocar or can extend proximally along the interior of the cutting cylinder 18.

While in its simplest form, as noted above, the filament of the invention may be simply looped in a single loop about the distalmost tip of the cutting cylinder with proximal ends of the loop fed through an aperture or apertures to extend proximally of the cylindrical tip, it is to be understood that various loop or knot configurations may be employed to various advantage in accordance with the invention. Indeed, as described more fully below, the invention may be utilized as a suturing device in which instance a loop which effects a knotting of the filament about the tissue may be preferred. Furthermore, as described more fully below, certain loop or knot configurations provide for a uniform radial cutting action and thus are currently most preferred.

Thus, as shown in FIGS. 4A–C, in accordance with a preferred embodiment of the invention, a half clove hitch type loop 30 is formed on the trocar 32 and employed to sever the tissue. In accordance with that embodiment of the invention, two apertures 34 are provided on opposite sides of the distal tip of the cutting trocar 32, one for receiving each end of the cutting filament 36. The filament 36 itself is looped into its operative configuration by passing the filament 36 or wire 1½ times or about 540 degrees about the distalmost tip of the trocar 32 as shown in FIG. 4A. As can be appreciated, when the proximal ends 38 of the filament 36 are pulled and the loop 30 passes off the distalmost tip of the cutting trocar 32, the loop 30 will gradually close from the outermost periphery inwardly as shown in FIG. 4B to thereby progressively radially sever the tissue. Severing the tissue in this manner effects less distortion of the tissue then a side-to-side cut which is effected by a loop with ends exiting on the same side of the distal tip. Furthermore, once the loop 30 has passed over the distal cutting tip of the trocar 32 and is being closed about the base of the specimen, the proximal ends 38 of the filament 36 can be alternately pulled back and forth to effect a cutting action on the squeezed, entrapped tissue to ensure full cutting. In that regard, the longitudinal ends 38 of the wire or filament 36 may be attached to a further element (not shown) which allows the operator to easily apply an alternating back and forth pressure first on one end, then on the other. As noted above, this will generate a sawing action by the loop 30.

As shown in FIG. 4C, the following complete severance of the tissue sample, the cutting filament 36 will extend across the diameter of the distal tip of the cutting trocar 32. Thus, the half clove hitch type loop has the further significant and unobvious advantage that the filament will provide a support for the tissue sample as the trocar 32 is removed from the body which maintains the tissue sample within the cutting trocar 32 until removal is desired. Further cutting action, as needed, after initial loop closure (FIGS. 4B and 4C) can also then be provided by rotating or twirling the trocar 32.

This "basketing" of the sample can be facilitated by providing a filament which includes a thicker or at least flatter portion and a thinner, sharper cutting portion. Once the tissue has been completely severed, then an end of the filament can be advanced to displace the cutting portion from adjacent the severed tissue sample and to place a thicker, flatter filament portion thereagainst to facilitate removing the tissue sample without damaging the same or disrupting the severed end.

In accordance with yet a further embodiment of the invention, illustrated in FIG. 5 in particular, first and second trocars 40, 42 are provided. One of the advantages of this configuration is that prior to actuation, the cutting loop 44 of filament 46 is disposed entirely within the instrument, between the trocars, so that it will not be displaced nor will itself disturb the tissue into which the assembly is being inserted.

In accordance with the invention, the inner and outer trocars 40, 42 are free from mechanical interconnection adjacent the distal tip to allow the loop 44 to pass distally of the inner, cutting trocar 40. The trocars can be at least partially coupled or interconnected at their proximal ends. Partial interconnection allows the insertion of an instrument for displacement of the loop 44 off the tip to facilitate closure of the loop 44, particularly where tissue enters the free air space between the trocars and obstructs initial movement of the wire off the tip. In the alternative, the inner and outer trocars 40, 42 can be mechanically interconnected adjacent the distal end but proximally of the loop 44 so as to define a chamber or compartment 48 adjacent to and proximal of the loop. Such a chamber can also advantageously be entirely within the inner and outer surfaces (within the wall) of either the inner or outer trocar or both. Such a chamber can be advantageously employed to define a passage for receipt of a gas such as nitrogen to chill or freeze the tissue sample, as described more fully below. In the alternative or in addition, an electrical wire can be fed between the trocars to convey electrical energy to the tip, for example to allow cauterization of the blood vessels. The wire used for cutting and retaining may also itself conduct electrical energy to enable heating or fulguration for electrocautery. Electric current controls and appropriate sheathing can be provided to enable fulguration, that is, to control bleeding during the cutting process.

Any medically approved cooling gas or liquid which is capable of reducing the temperature of the tissue sample, for example to below 0° C., to cool or freeze the tissue may be used as the trocar coolant. In that regard, various halogenated hydrocarbons or liquid nitrogen may be appropriate. Of course, as noted above, a biopsy instrument having coolant circulated therewithin must be configured so as to ensure no leakage particularly in the region of tissue penetration. Such can be accomplished by sealing and mechanically joining the trocars adjacent the distal end, proximally of the mounted loop or, in the alternative, by providing a closed circulation path for the coolant between the inner and outer trocars.

In accordance with yet a further aspect of the invention, one or more optical fibers (not shown in particular) are disposed within the walls of either trocar or between the inner and outer trocars. Laser light directed through and along such optical fibers can be used, for example to cauterize the side walls of the biopsied cylinder. A potential alternative is to direct laser light through the cutting filament to achieve cauterization at the distal cut surface of the tissue.

Yet a further alternative is that the wall of the inner trocar may be hollow so as to allow flow of coolant and/or placement of temperature probes, optical fibers, and the like. Thus, the inner and outer trocars described above could be simply inner and outer walls of a double walled trocar structure.

However, by forming the assembly of the invention as two separate trocar elements 40, 42, the advantageous reusable characteristics of the invention may be more fully realized. Indeed, the outer coring trocar 42 can be maintained in place within the body while the inner cutting or biopsy receiving trocar 40 can be removed and replaced so that a further, even deeper tissue sample can be obtained without retraversing the outer tissue layers. A further advantage of this embodiment is that other instruments can be easily introduced through the outer, coring trocar 42, such as small endoscope, electric fulguration or laser probes, and syringe-type drug delivery applicators to effect hemostasis and the like.

The inner and outer trocars 40, 42 are preferably hollow as shown so that an obturator or stylet (not shown in FIG. 5) can be inserted through the outer trocar 42 or through the assembled inner and outer trocars. Thus, an obturator or stylet can be provided for initial insertion to the desired locus of the biopsy. The obturator can then be removed from the outer trocar 42 and, if not provided in combination with the outer trocar, the inner, cutting trocar 40 with the cutting wire 44 looped thereabout inserted into the outer coring trocar 42. The combination of the coring and cutting trocar 40, 42 can be then advanced or simply the coring trocar 42 advanced so as to obtain a tissue sample. Preferably, the assembly is advanced so as to minimize the likelihood that the loop will be disrupted by the tissue surrounding the sample.

Significantly, the prior art lacks an appreciation for the necessity of an accelerating effect as being necessary or advantageous to cutting. Indeed, applicant has found that initial acceleration may be vital to a clean, precise cut. More particularly, one almost never begins to cut right at the surface of the object to be sliced. An effective slice/cutting action nearly always includes an acceleration step into that object to initiate the cutting process to overcome the initial resistance to cutting, primarily due to surface tension.

As noted above, the tip of the cutting trocar can be inclined so as to facilitate movement of the loop over the distal edge to engage the tissue. As also noted above, such a configuration can advantageously facilitate an accelerated motion of the filament in contact with the tissue thereby ensuring smooth severance thereof.

As an alternative, in accordance with a preferred embodiment of the invention, the distalmost tip of the trocar is formed from a material which can flex inwardly, particularly when sufficient pressure is applied thereto. The flexible tip can either be formed from a material which gives in response to the application of a predetermined force or the tip can be defined from one or more tabs or flaps which give upon application of a predetermined force thereby releasing the wire to impinge upon the distal margin of the specimen with sufficient force to cleanly slice the same.

Thus, in accordance with a further alternate embodiment of the invention which is illustrated in particular in FIG. 6A, the acceleration of the cutting filament 50 can be facilitated or enabled by the provision of a plurality of flexible tabs 52 at the distalmost end of the cutting trocar 54 which are selectively deflected upon application of a sufficient force to the cutting wire 50, thereby suddenly releasing the same into contact with the tissue ensuring clean cutting and complete severance thereof.

More particularly, a plurality of tabs 52, for example between 3 and 8, are evenly distributed about the circumference of the inner trocar 54 end. The cutting wire or filament 50 is looped about the tabs 52 to define a half clove hitch type loop 56. The outside coring trocar 58 is placed relative to the inner trocar 54 so that its cutting tip is in proximity to and preferably actually shields the open V sections 53 between the adjacent tabs of the inner trocar. Where release tabs 52 as shown in FIG. 6 are provided, the filament 56 is preferably fed through holes 60 in the outer trocar 58 so that as the ends of the filament 50 are pulled, the loop 56 will not cause complete collapse of the release tabs 52 (as can occur if the holes 60 are located within tabs 52 or at V sections 53) and the finally remaining filament strand will extend between the rigid side walls at the distalmost tip of the outer trocar 58. Apertures in the inner trocar for receiving the filament could, of course, be provided particularly where it is deemed necessary or desirable for the filament to hold or support the tissue sample in the inner trocar during its removal from the outer trocar. Clearly when the inner and outer trocars are simultaneously removed from the body, attachment and feed of the filament to and though the outer trocar is sufficient and may be preferred. Advantageously, furthermore, when the filament passes through openings in the outer trocar, relooping of the filament in situ is possible, as discussed more fully below.

Figure 6B:
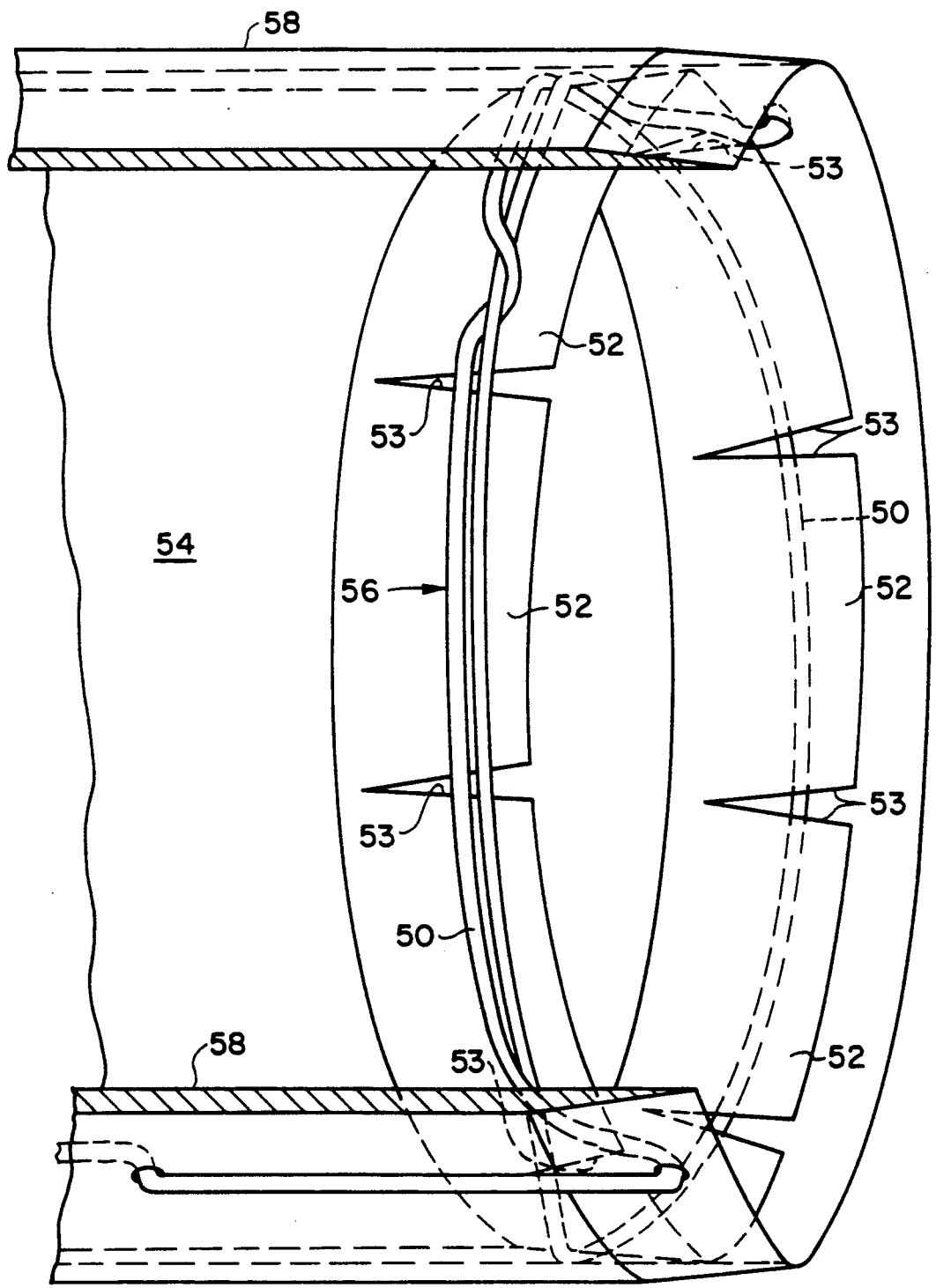
FIG. 6B is a view similar to FIG. 6A but with the filament crossed on itself so that the filament will knot.

As shown in FIGS. 6A and 6B, the tabs preferably arch slightly outwardly into engagement with the inner wall of the outer, coring trocar to ensure smooth and complete receipt of the cored tissue. When the tabs arch outwardly in this manner, the filament is preferably threaded through opposite V sections 53 to the holes 60, as shown. Where the tabs are flared, suitable means such as ribs (not shown) can be provided to prevent the loop from slipping proximally, particularly when the filament is tensioned.

Thus, as tension is applied to the proximal ends of the filament 50, the filament 50 will be drawn radially inwardly and slightly forwardly (distally) with respect to the release tabs 52. When a sufficient force is applied to the filament 50, the release tabs 52 will flex radially inwardly thereby suddenly releasing the cutting filament 50. The filament 50 as looped is then free to sever the tissue adjacent the distalmost end of the inner trocar 54 and ultimately a single filament or strand extends between the openings 60 on opposite sides of the outer trocar 58. Furthermore, as shown in particular in FIG. 7, the inwardly flexed tabs will provide greater assurance of retaining the specimen and will tend to encourage the loop to close closely adjacent the ends of the tabs. Indeed, by pinching the tissue a bit as shown in FIG. 7, the tabs create a funnel shape in the attached tissue which in turn guides the loop to the neck of the tissue segment, adjacent the tabs. The amount of tissue necking by the tabs of course depends upon the tissue being sampled and may therefore occur to a greater or lesser extent than shown in FIG. 7.

Any suitable means can be provided to enable flexure of the distalmost tip of the inner, tissue-receiving trocar. As mentioned above, a flexible material can be employed which will upon application of sufficient force, flex and allow the loop to slide off the cutting trocar. Another alternative which was also described above is the provision of a plurality of tabs which are deflectable relative to the remainder of the trocar body. Yet a further alternative is to provide a cutting trocar having distal tabs defined by two or more layers of metal material wherein one metal will expand faster and/or to a greater extent than the other when heated. The divergent rates of expansion result in flexing of one or more of the tabs. Thus, the tab(s) can be heated as a force is applied to close the loop of wire. As the tabs begin to flex and the tension in the wire increases, the loop will be released from the tip of the trocar and impinge upon and sever the tissue.

In accordance with yet a further aspect of the invention, it is possible to reload the half clove hitch type loop configuration with the inner and outer trocar combination illustrated in particular in FIG. 6A. Of course, a repeat loading capability would allow removal of multiple polyps, taking multiple biopsies, multiple hair transplants, plastic surgery, etc.

After retracting the wire 50 and cutting the deepest end of the tissue sample, the wire 50 will be disposed across the distal end opening of the outer trocar 58 and the release tabs 52 of the inner trocar 54 will be deflected inwardly. If the tabs are disposed so as to at least partially cross the center line of the trocar assembly, then advancing the inner trocar 54 relative to the outer trocar 58 will deflect the wire 50 outwardly to the outer surface of the inner trocar 54. The tabs 52 can then be flexed outwardly to their proper orientation by inserting an appropriately sized obturator or the like (not shown) through the inner trocar 54. Where the release tabs 52 do not extend across the mid line of the trocar assembly, then an obturator (not shown) can be inserted through the inner trocar 54, to both deflect the wire 50 to the side and reset the tabs 52. Subsequent advancement of the inner trocar 54 will thus properly dispose the wire 50 on the exterior surface of the inner trocar 54. A hook or the like is then advanced between the inner and outer trocars into engagement with the wire 50 to hold it against the outer wall of the inner trocar 54. By holding the wire 50 against the inner trocar 54 and then twirling either the inner or the outer trocar through 360° relative to the other, a half clove hitch type loop 56 will be reestablished on the outer circumference of the inner trocar 54. A similar reloading process can be effected with the temperature sensitive tabs discussed above.

The tissue can be frozen concurrently with biopsy, as noted above, essentially eliminating any bleeding from the severed peripheral organ vasculature. In the alternative, the tissue can be frozen prior to the biopsy cutting process. Indeed, prior to the use of the retriever of the invention, a cryoprobe can be inserted into the tissue of interest. A frozen cylinder of tissue will thus be disposed in surrounding relationship to the probe. With current technology, a frozen cylinder of up to about 2 cm in width can be created. The trocar of the invention can be advanced so as to cut and sever the frozen core from the surrounding tissue. In that regard it is not anticipated that the cutting action of the loop provided in accordance with the invention will be significantly hindered by the fact that frozen or semi-frozen tissue is being severed. However, there may be a greater need for the back and forth or sawing motion discussed above.

In accordance with yet another aspect of the invention, a relatively fine cutting wire 62 disposed across the distal cutting path of the trocar 64 can advantageously be provided to obtain a sample of tissue in the form of two equal semi-cylinder segments that can be used for separate evaluation. As shown in FIG. 8, the wire 62 used with the double biopsy trocar 64 preferably has a triangular configuration so as to present a forward cutting edge and a flat rear edge for facilitating retention of the tissue samples without further disruption. With that instrument, direct penetration of the trocar 64 is effected without a twirling or rotational motion. Once the instrument has been fully inserted, the trocar 64 can be twirled to cut the base of the tissue sample. The final radial disposition of the wire 62 is preferably offset from the initial cutting orientation so that the wire 62 can be used to help retain and retrieve of both semi-cylindrical samples of tissue. Indicia can be provided on the proximal end of the instrument to ensure proper disposition for removal or to otherwise allow the practitioner to readily determine the location of the filament 62.

Conventional cutting of biopsy specimens is typically done outside of the body. Moreover, cutting is generally that of a frozen core, not of fresh, much less in vivo tissue as is possible with the invention. With the instrument illustrated in FIG. 8, comparable biopsies can be taken concurrently intraoperatively.

Yet a further application of the trocar device of the invention is to ligate or suture the tissue and vessels. Indeed, where a non-cutting wire or filament is mounted to the distal tip of the trocar, whether in the form of a loop as shown in FIGS. 2 and 3 or a half clove hitch type loop of the type shown in FIGS. 4A–4C, pulling the filament will form a knot in surrounding relation to the base of the tissue which extends into the instrument. Thus, as shown by way of example in FIG. 6B, a non-cutting filament can be looped around the inner trocar and crossed over itself, much like tying a shoe lace. When the proximal end or ends of the filament are tensioned, the tabs will flex inwardly, and the loop will be released into engagement with the tissue. Further pulling the filament will tighten the knot about the tissue segment. Such knots can suitably be used for hemostasis and for creating tissue-to-tissue adhesion.

In accordance with the invention, a second half clove hitch type or similar loop, for example, can be defined about the distal tip of the cutting trocar. The same or different exit holes can be used for the second loop. The first wire or filament is provided so as to effect a hemostatically effective knot. The second wire can then be actuated to remove the tissue segment proximal to the suturing knot. In the alternative, two different inner trocars with different filaments could be introduced sequentially.

The trocar of the invention can also be advantageously employed in various aspects of plastic surgery and dermatology. Indeed, with the instrument of the invention, a skin graft of precise shape and size as well as depth can be carved and transferred to another locus. For example, if a 1 cm cavity results from the removal of a small skin lesion (potentially with an instrument formed in accordance with the invention), removed diseased tissue could be replaced by a suitable plug of good skin such as a 1 cm wide circle of full or split thickness epidermis which has been excised in accordance with the invention.

This technique could also be advantageously applied in hair transplant surgery. Indeed, an entire hair follicle could be collected, removed and applied to another location with the retriever of the invention. In accordance with such an application of the concept of the invention, where a half clove hitch type loop is used the filament or wire should be removed by, for example, pulling one end, to allow the tissue plug to be removed at the desired location. Further, removal of the tissue segment can be facilitated by inserting a probe or the like into and through the inner or cutting trocar to urge the t issue segment distally, out of the trocar.

Any of the foregoing instruments of the invention can be advantageously loaded and sterilized prior to use, individually or as a kit. Thus, an entire assembly, including cutting trocar, wire, and outer trocar, if provided, can be sterilized, for example, autoclaved, prior to use and stored in a sterile package. As an alternative or in addition, the tip can have a fitted plastic insert or cover which will keep the wire or cutting filament clean and in place prior to use.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A trocar element having a longitudinal axis, a proximal end, a distal end, a passage therein extending from said distal end toward said proximal end along at least a portion of said longitudinal axis, and a filament looped about an exterior surface of said distal end, said filament having at least one longitudinal end extending proximally from said distal end whereby the application of a force to said least one longitudinal end causes said loop to slip off of said distal end and further application of force to said at least one longitudinal end causes said loop to at least partially close adjacent said distal end.

2. A trocar element as in claim 1, further comprising at least one aperture defined through a wall of said trocar element adjacent said distal end, said at least one longitudinal end of said filament being threaded through said aperture.

3. A trocar element as in claim 2, where said distal end is inclined so as to have a distal portion and a distalmost tip, said aperture being defined adjacent said distalmost tip, so that as said loop slips off the distal end, it first slips off the distal portion and ultimately closes adjacent said distalmost tip.

4. A trocar element as in claim 1, in combination with an outer trocar member mounted in coaxial surrounding relation to said trocar element, said outer trocar member having a longitudinal axis, a proximal end, a distal end and a passage defined along at least a portion of the length thereof from said distal end toward said proximal end thereof, said passage being sized so as to receive said trocar element.

5. The combination of claim 4, further comprising at least one aperture defined through a wall of said outer trocar element adjacent said distal end thereof, said at least one longitudinal end of said filament being threaded through said aperture.

6. The combination of claim 4, further comprising means for cooling said trocar element.

7. The combination of claim 4, wherein said loop extends about 540 degrees around said distal end of said trocar element.

8. The combination of claim 7, further comprising first and second apertures defined through a wall of said outer trocar member adjacent said distal end, each longitudinal end of said filament being threaded through a respective said aperture.

9. A trocar element as in claim 7, wherein at least a portion of said distal end of said trocar element is able to flex relative to said longitudinal axis so as to facilitate accelerated release of said filament when said at least one longitudinal end is tensioned.

10. The combination of claim 9, further comprising first and second apertures defined through a wall of said outer trocar member adjacent said distal end, each longitudinal end of said filament being threaded through a respective said aperture.

11. A trocar element as in claim 10, further comprising first and second apertures defined through a wall of said trocar element adjacent said distal end, each longitudinal end of said filament being threaded through a respective said aperture.

12. The combination of claim 9, wherein the distal end of said trocar element comprises a plurality of flexible tabs, said filament being mounted in surrounding relation to said flexible tabs so that when a predetermined force is applied to said at least one longitudinal end of said filament, said tabs will flex and release said filament.

13. The trocar element of claim 1, in combination with an obturator element having a sharp distalmost tip, said obturator element being coaxially disposed within said trocar element and axially moveable with respect thereto so as to selectively protrude from said distal end of said trocar element.

14. A trocar element as in claim 1, wherein said loop extends about 540 degrees around said distal end.

15. A trocar element as in claim 1, wherein said filament is a single strand of material.

16. A trocar element as in claim 1, wherein said filament has a round cross-section.

17. A trocar element as in claim 1, wherein said filament has a triangular cross-section.

18. A trocar element as in claim 1, wherein at least a portion of said distal end is able to flex relative to said longitudinal axis so as to facilitate accelerated release of said filament when said at least one longitudinal end is tensioned.

19. A trocar element as in claim 1, wherein said filament is segmented to have at least two portions having different cross-sectional configurations.

20. An inner trocar element having a longitudinal axis, a proximal end, a distal end, a passage therein extending from said distal end toward said proximal end along at least a portion of said longitudinal axis, an outer trocar element disposed in surrounding relation to said inner trocar element, said outer trocar element having a proximal end, a distal end, and a longitudinal axis, and a filament extending from an exterior side surface of said outer trocar element at least across a diameter of an opening of said passage at said distal end of said inner trocar element whereby tissue can be excised by inserting said inner and outer trocar elements into a target tissue and then rotating at least one of said inner and outer trocar elements.

21. A trocar element as in claim 20, wherein said filament has a triangular cross-section.

22. A trocar element as in claim 20, wherein said filament is segmented to have at least two portions having different cross-sectional configurations.

* * * * *